US005240755A

United States Patent [19]

Zimmer

[11] Patent Number: 5,240,755

[45] Date of Patent: Aug. 31, 1993

[54] PERFORATED LABEL WEB AND METHOD OF PRODUCING SUCH WEB

[75] Inventor: Gregory Zimmer, Franklin Lakes, N.J.

[73] Assignee: Zimmer Industries, Inc., Hawthorne, N.J.

[21] Appl. No.: 690,859

[22] Filed: Apr. 23, 1991

[51] Int. Cl.[5] .................... A61F 13/02

[52] U.S. Cl. .................... 428/40; 40/299; 83/660; 206/813; 206/820; 428/42; 428/43; 428/136; 428/220

[58] Field of Search .................... 428/40, 43, 42, 136, 428/220; 206/813, 820; 40/299; 83/660

[56] References Cited

U.S. PATENT DOCUMENTS

| | | | |
|---|---|---|---|
| 2,264,339 | 12/1941 | Sherman | 156/257 |
| 3,892,901 | 7/1975 | Smith | 40/299 |
| 3,920,122 | 11/1975 | Koehlinger | 428/43 |
| 4,889,731 | 12/1989 | Williams | 206/469 |
| 4,925,716 | 5/1990 | Haas | 428/43 |
| 4,951,967 | 8/1990 | Michalik | 428/43 |
| 5,114,771 | 5/1992 | Ogg | 428/43 |

*Primary Examiner*—George F. Lesmes
*Assistant Examiner*—Nasser Ahmad
*Attorney, Agent, or Firm*—Brooks Haidt Haffner & Delahunty

[57] ABSTRACT

Labels and a label web without a carrier web which labels are formed by perforating a web with a perforator having 20–120 spaced teeth per inch and which provide ties securing the label to the web which have a maximum dimension in the direction of the label periphery of 0.007 inch so that when the label is removed from the web the ties are not visible to the naked eye. At least 50% of the web is perforated along the label periphery to ease removal of the labels from the web, but a sufficient number of ties is retained, depending on the strength of the web material and the pulling force required, to retain the label attached to the web during pulling of the web for further processing.

15 Claims, 3 Drawing Sheets

PERFORATED LABEL WEB AND METHOD OF PRODUCING SUCH WEB

FIELD OF THE INVENTION

The invention relates to the partial cutting of labels from a web in a manner and by apparatus which will cause the edges of labels removed from the web to appear to the naked eye to have been cut by a die with a continuous cutting edge and relates to a label web and the label so obtained.

BACKGROUND OF THE INVENTION

In a conventional method of cutting labels from a web, a web, which may be made of paper, plastic, etc. is carried by a carrier web. The surface of the label web facing the carrier web has an adhesive thereon, and normally, the carrier web is treated with a release agent, such as silicone, to ease the peeling of the cut label from the carrier web.

The label web is cut with the desired shape of the label by a die with a continuous cutting edge so that the label, after removal from the label web, has smooth continuous edges which are pleasing in appearance and which are considered the most desirable in the label industry. However, the label web must be transported from the cutting apparatus, usually by pulling the web, to other apparatus, and the carrier web is needed not only to shield the adhesive but also to provide the strength necessary for such pulling and to prevent the cut labels from falling out of the label web. Such other apparatus can merely be a take-up roll from which the label web is supplied to further apparatus or the label web may be supplied directly to such further apparatus. Such further apparatus normally includes label removing and applying apparatus and can include label printing apparatus.

The carrier web can represent 40–60% of the cost of the material of the combined web and normally is discarded after the labels are removed. Furthermore, if the carrier web has been treated with silicone as a release agent, the carrier web cannot be recycled.

Accordingly, it is desirable to be able to eliminate use of the carrier web and still permit the label web to be processed, after it is cut, with conventional apparatus. However, to be commercially acceptable, the edges of the cut labels must have an appearance which, to the naked eye, is substantially the same as a label which has been cut with a die with a continuous cutting edge.

One attempt to solve such problem is described in U.S. Pat. No. 3,920,122. In such patent, it is proposed that the continuous cutting edge of a cutting die be deformed or nicked at spaced portions so that there are cut-through portions of the label web spaced by bridges of uncut web which taper so that they are narrower at the label ends thereof. The width of the bridges at the label end is in the range from 0.015 in. to 0.045 in. and at the remnant end is in the range from 0.027 in. to 0.055 in. On the other hand, it is admitted in the patent that when the label is removed from the web, the bridges tear apart at some point between the connection of the bridge to the label and to the web remnant and a portion of the bridge will remain at the label edges. Thus, the dimension of the remaining portion of the bridge in the length direction of the label edge can be from 0.015 in. to 0.055 in. A remaining portion of such dimension is visible to the naked eye, and the patent indicates that such objectionable feature is offset by reason of the depression formed in the label edge and extending in the direction of the length of the web. Accordingly, not only does the appearance of the label edge not conform to the appearance of a die cut edge, but also a specially and difficultly formed die must be used.

BRIEF SUMMARY OF THE INVENTION

So-called "microtooth" perforators, or perforating dies, are known in the art and have 20–120 teeth per inch. In accordance with the invention, such a perforator with a particular spacing and height of the teeth is used to perforate a label web without a carrier web to provide label edges which are substantially indistinguishable by the naked eye from label edges cut by a die having a continuous cutting edge. The perforator has a number of teeth in the range from 20–120 teeth per inch, preferably, at least 50 teeth per inch, the teeth are spaced so that at least 50% of the label web along the label edges are cut and so that, in the preferred embodiment, the width of the "bridges" or "ties" does not exceed 0.006 in. and the height of the teeth is such that the teeth penetrate the label web and any adhesive thereon without creasing the web.

DETAILED DESCRIPTION OF PREFERRED EMBODIMENTS

Figure 1:
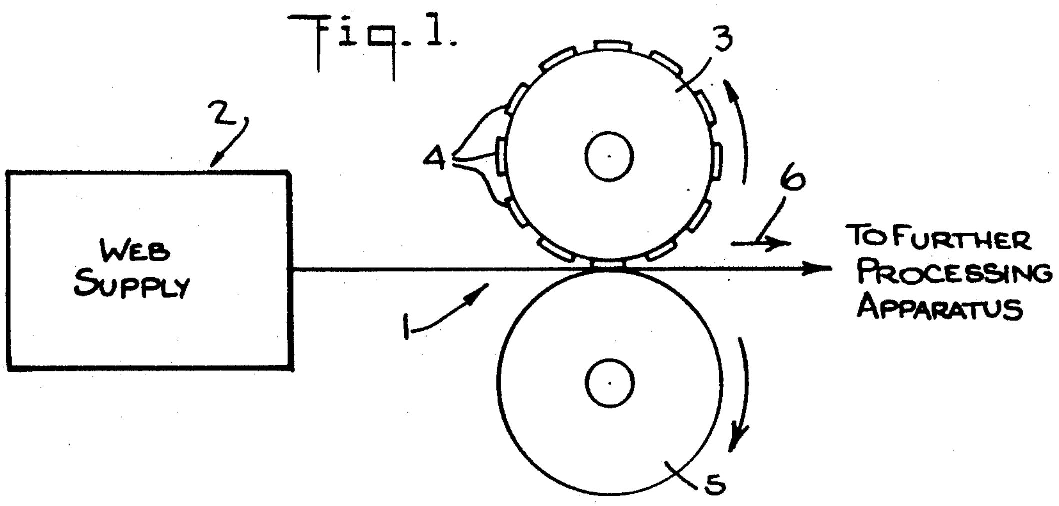
FIG. 1 is a schematic diagram of apparatus for producing the label web of the invention.
Figure 2:
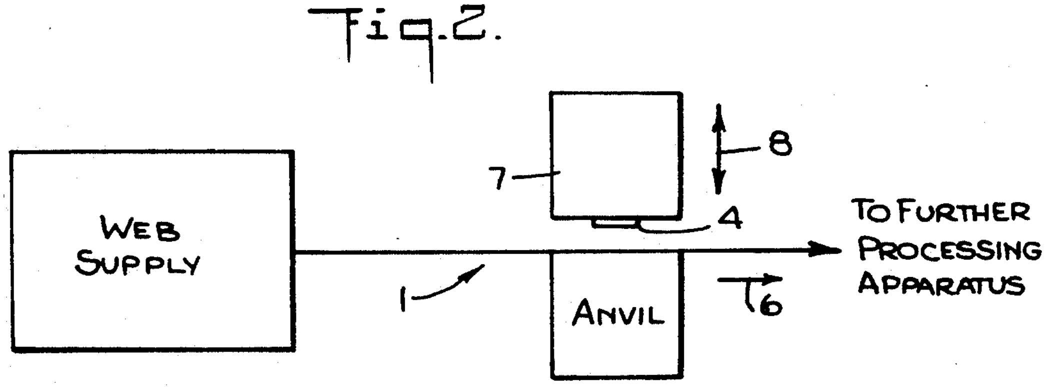
FIG. 2 is a schematic diagram of an alternative form of apparatus for producing the label web of the invention.

FIGS. 1 and 2 illustrate schematically apparatus for performing the perforation of a label web which corresponds to apparatus for die cutting, with a continuous cutting edge, except for the fact that the label web is not carried by a carrier web.

Thus, as illustrated in FIG. 1, a label web 1 without a carrier web, but which can have an adhesive on the lower surface thereof which is activated in the later stage of the label processing, e.g., a thermally activated adhesive, or which can be without an adhesive at the lower surface thereof, the necessary adhesive being applied after the web is perforated, and which can have, at the upper surface thereof, a "piggy back" label web as described hereinafter, is supplied from a source 2 of the web 1 to a pair of rolls, a roll 3 carrying a plurality of perforators 4 and a platen roll 5. The web source 2 may be a roll of web label stock, either printed or without printing.

After passing between the rolls 3 and 4, where the web 1 is perforated with the outline of the desired label by the perforators 4, the web 1 is supplied to a take-up roll or to further processing apparatus, such as label removal and applying apparatus, and if adhesive has not been applied to the lower surface of the web 1 and printing has not been applied to the upper surface of the web 1, to the apparatus necessary to apply the adhesive or the printing to the labels on the web before the labels are applied to an object, such as a container.

In the apparatus of FIG. 1, the web 1 is pulled continuously in the direction of the arrow 6 and the material of the web 1 with the perforations produced by the perforators 4 must have sufficient strength to withstand such pull which normally means that on the order of 25% to 50% of the web material is retained between the perforations. Also, the material between the perforations must prevent the label portions of the web from falling out of the web.

In the apparatus of FIG. 2 which can have a perforator 4 which is the same as the perforators 4 or which can be a steel rule with teeth, the web 1 is moved stepwise in the direction of the arrow 6 and a perforator support 7 is reciprocated in the directions of the double-ended arrow 8. The web 1 is received between the support 7 and an anvil 9 where, when advancing of the web 1 stops, the support 7 lowers and causes perforation of the web 1 in the outline of the perforator 4.

Figure 3:
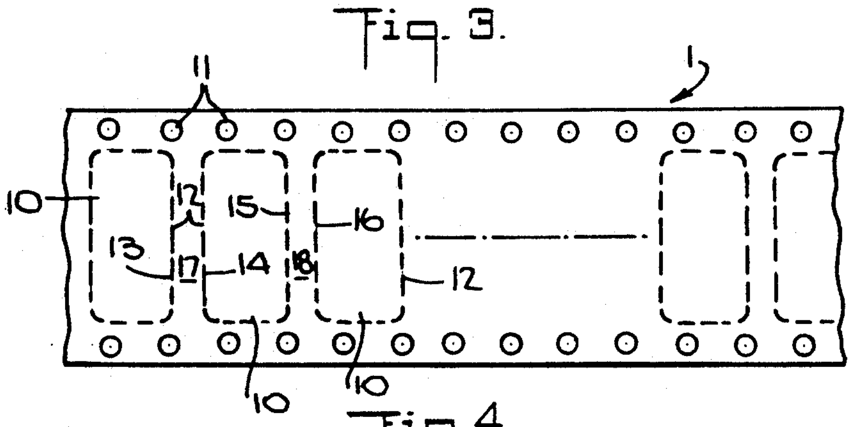
FIG. 3 is a plan view of one embodiment of the label web of the invention.

FIG. 3 illustrates the use of the invention in producing labels 10 on an elongated web 1 of a conventional kind, i.e. paper or plastic, having indexing holes 11 for purposes known in the art. Thus, the labels 10 are portions of the web 1 which have been outlined by perforations 12 and which are disposed relative to each other in the direction of the length of the web 1. The portions of the web 1 at the sides of the label portions and in between the label portions are remnant portions remaining after the label portions are removed and can be recycled since they are not treated with a release agent, such as silicone. The outline of the label portions can be of any desired shape, e.g. rectangular as shown, oval, circular, etc., to which the base of the perforator and the teeth thereon can be formed. This usually is limited by the radius to which the teeth can be formed on a planar base or in the event that they are on a steel rule, the radius to which the steel rule can be bent.

With the method of the invention, the leading and trailing edges of the label portions can coincide thereby eliminating the web remnant between label portions. Thus, the edges 13 and 14 can coincide, the edges 15 and 16 can coincide, etc. and the web remnants 17, 18, etc. can be eliminated.

Figure 4:
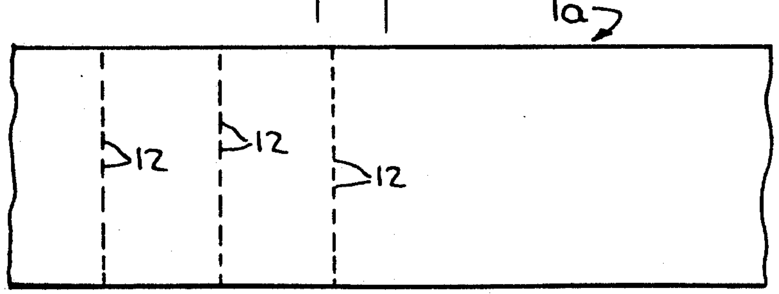
FIG. 4 is a plan view of an alternative embodiment of the label web of the invention.

If it is not necessary to retain web material at the sides of the label portions, e.g. for indexing, the web 1*a* (FIG. 4) can be perforated transversely of its length thereby eliminating all remnant portions of the web.

Figure 5:
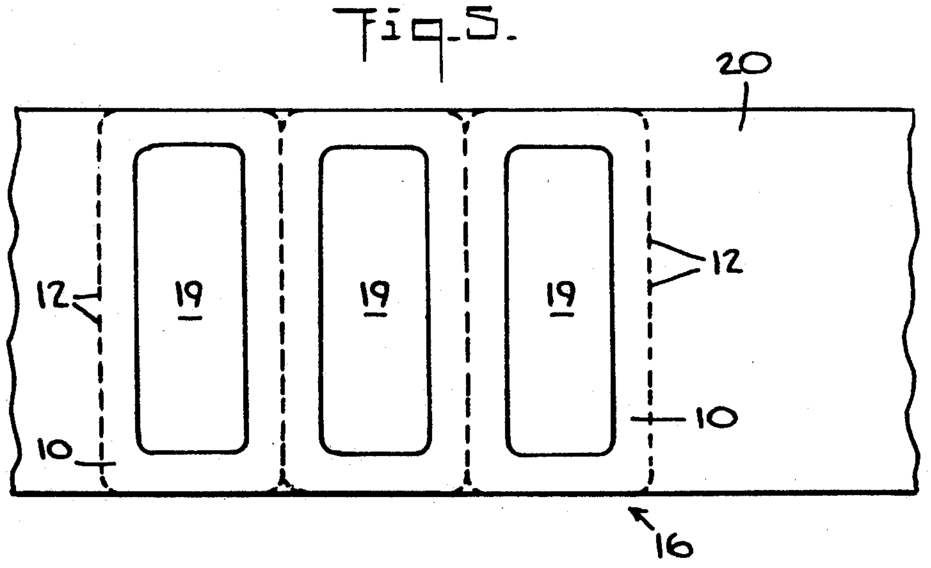
FIGS. 5 and 6 are, respectively, plan and side views of an alternative embodiment of the label web of the invention.
Figure 6:
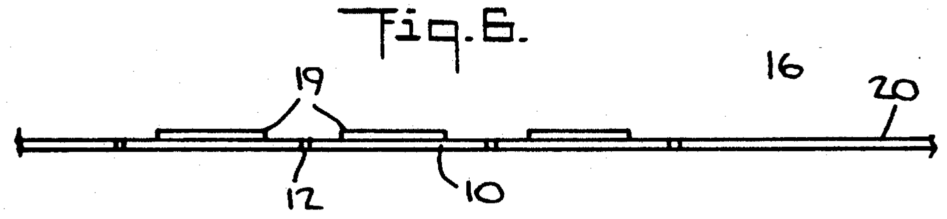

If it is desired to form a web with what is called a "piggy back" label as illustrated in FIGS. 5 and 6, a multi-level perforator or combined perforator and continuous die, described hereinafter in connection with FIG. 15, can be used in conjunction with a two-layer web lb which, as illustrated in FIGS. 5 and 6, has the remnants of the upper or "piggy back" layer removed for ease in illustration. The upper label portions 19, which, preferably are cut with a continuous edge die, but which can be formed by a perforator, are secured to the lower label web 20 by an adhesive which permits peeling of the label portions 19 from the web 20 with the adhesive remaining on the backs of the label portions 19 so that the removed label portions 19 may be applied and adhere to another object such as a business form.

However, the lower web 20 is perforated around each of the label portions 19 with the perforations 12 so that as the label portions 19 are removed, the label portions 10 of the lower web 20 are simultaneously removed, and normally, the two label portions, with an adhesive at the back of the portion 10 are applied to an object. At some time thereafter, the label portion 19 is removed from the label portion 10.

Figure 7:
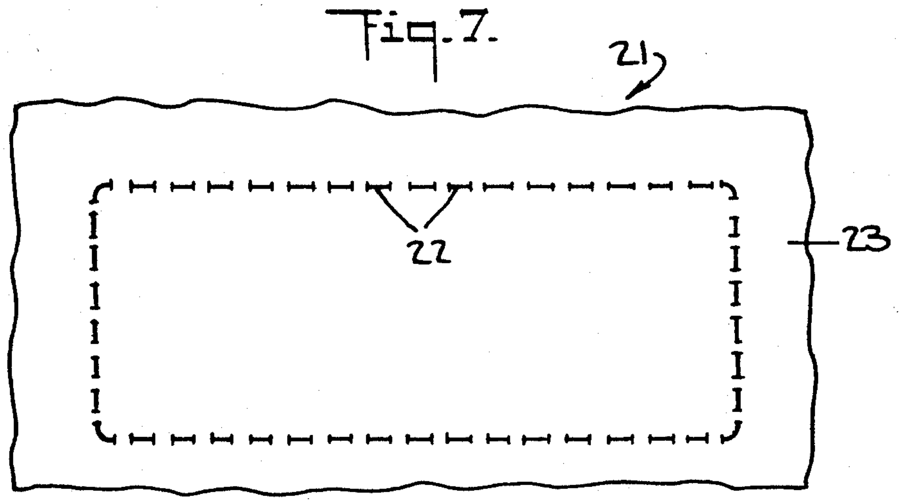
FIG. 7 is a bottom view of a portion of a perforator shown in FIGS. 1 and 2.

FIG. 7 illustrates a perforator 21 with the perforating teeth 22 extending from a base plate 23 which can be a flexible metal sheet. The perforator 21 can be used to form label portions 10 of the shape illustrated in FIG. 3.

Figure 8:
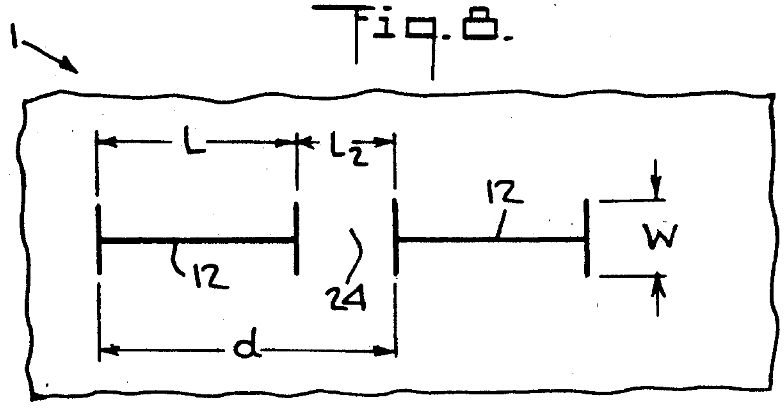
FIG. 8 illustrates a pair of adjacent perforations of the type produced by the perforator illustrated in FIG. 7.

The teeth 22 can have various shapes which will produce the perforations 12 as shown in FIG. 8. Thus, the teeth 22 preferably are shaped so that material of the web 1 is not punched out and instead, is merely slit in the shape of an I lying horizontally, that is with the segment thereof interconnecting the end segments thereof extending transversely to the length of the web. In this way, depending on the tearing of the unperforated portions upon removal of a label, the remaining portions at the perforations will have a height substantially equal to the height of the adjacent torn portions.

With reference to FIG. 8, the length L, of a perforation preferably is 50% of the distance d, that is, at least equal to 50% of the distance between corresponding ends of the perforations for ease in removal of the label, or label portion, 10 from the web 1. The length L, depends on the strength and thickness of the web material and for light paper stock should be closer to 50% of d whereas for stronger material, such as Mylar, can be 75% of d. The width W, at the ends of a perforation preferably, is in the range from 0.010 inch to not greater than about 0.028 inch.

Between pairs of perforations 12, there are ties 24 of web material which have a length $L_2$ not greater than 0.007 inch and preferably in the range from 0.004 to 0.006 inch. Generally speaking, the length $L_2$ should be equal to about 80% of the thickness of paper stock, e.g. for what is known as light paper having a thickness of about 0.006 inch, the length $L_2$ would be about 0.005 inch. The ties 24 have the purpose of preventing the unsupported label portions 10 from falling out of the web 1, 1*a* or 1*b* and permitting the web to be pulled through the perforating station and in further processing apparatus.

Figure 9:
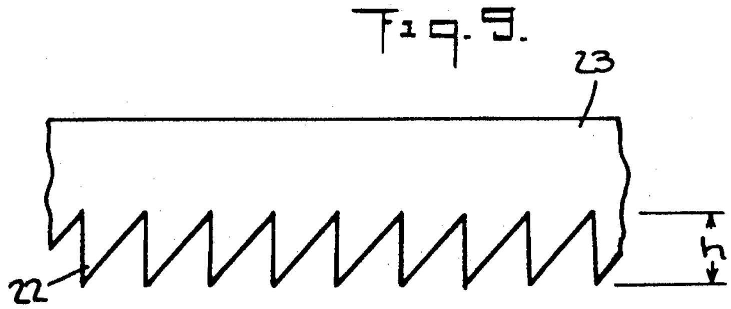
FIGS. 9, 10 and 11 are enlarged, side elevation views of perforation teeth shapes which can be used for the perforator of the invention.
Figure 10:
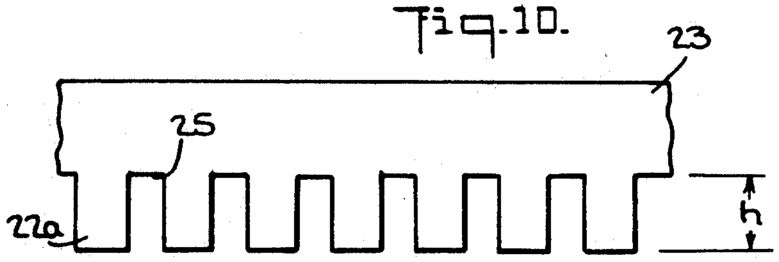
Figure 11:
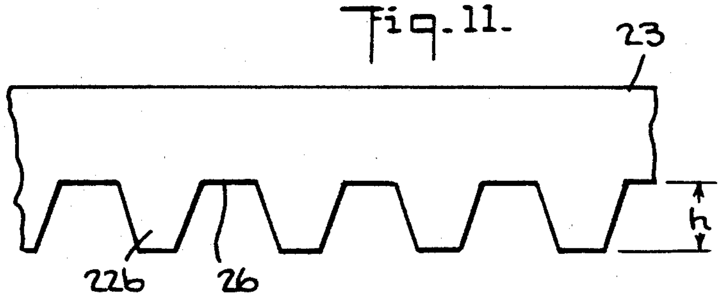

As shown in greatly enlarged scale in FIGS. 9–11 the teeth 22 can have various shapes as viewed transversely to the row of teeth. For example, the teeth 22 in FIG. 9 have the shape of a saw-tooth, the teeth 22*a* in FIG. 10 are rectangular and the teeth 22*b* in FIG. 11 are trapezoidal.

The height h of the teeth from the base plate 23 is at least equal to the thickness of the web being perforated and if the web has adhesive at its lower surface, at least equal to the thickness of the web plus the thickness of the adhesive so that the web, and the web plus adhesive, is penetrated by the teeth without creasing the web by portions of the base 23, such as the portions 25 and 26, between the teeth. Accordingly, for tolerance reasons, the height h will be slightly greater than the thickness of the web or the thickness of the web plus the thickness of the adhesive.

Figure 12:
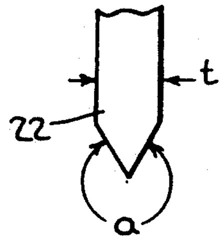
FIG. 12 is an enlarged side view of a preferred shape for a tooth of the perforator.
Figure 13:
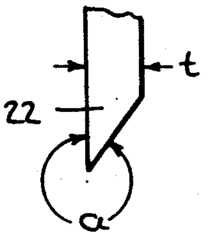
FIG. 13 is an enlarged side view of another shape for a tooth of the perforator.

As illustrated in FIGS. 12 and 13, the teeth, when viewed from the direction at right angles to the view of FIGS. 9–11 can have various shapes which will provide the desired perforating action. Thus as shown in FIG. 12, the teeth 22, and hence the teeth 22*a* and 22*b*, can have a wedge or V shape. The thickness t can be on the order of 0.028 to 0.056 inch and the angle a can be on the order of 60°. Similarly, the teeth 22, or the teeth 22*a* and 22*b*, can have a chisel shape, as shown in FIG. 13, the thickness t and the angle a being the same as for FIG. 12. Of course, as will be apparent from the consideration of the width W desired for ends of the perforation 12, the teeth will not be caused to penetrate the web until the portion of thickness t reaches the upper surface of the web unless the thickness t is 0.028 or less so that the width W will be 0.028 and preferably, less.

Figure 14:
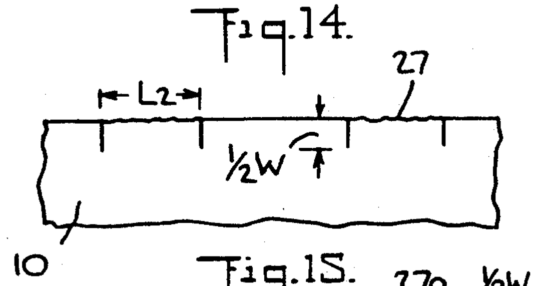
FIGS. 14–16 are greatly enlarged, magnified, plan views of the edge of a label produced in accordance with the invention.
Figure 15:
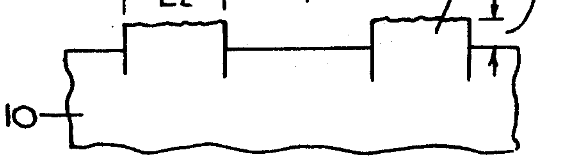
Figure 16:
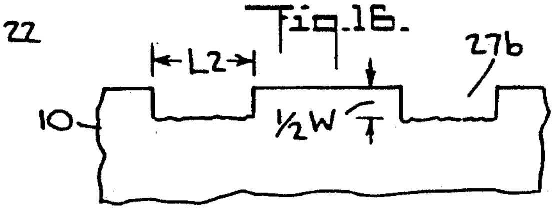

FIGS. 14, 15 and 16 are a magnified, enlarged, fragmentary, plan views of a label 10 after it has been removed from the web. It will be apparent that when the ties 24 tear upon removal of a label 10 from the web, the ties 24 can tear at any portion thereof and the tear line is not necessarily parallel to the label edge. However, the tear line will normally be within the limits of the width W of the perforation ends. FIG. 14 illustrates the ideal case where the tie 24 tears along a line co-linear with the adajcent edge portions of the label edge. FIGS. 15 and 16 illustrate the extremes of the tear lines, and the amount that the tear line departs from co-linearity with the adjacent portions of the label edge will substantially never exceed ½ W, or 0.014 inch, and usually will be less. Accordingly, the edge of the label 10 can have a series of projections 27 or 27*a* which are the remnants of the ties 24 after the label 10 is removed from the web or gaps 27*b* or a mixture of projections and gaps. The projections 27 and 27*a* and the gaps 27*b* have a length $L_2$ in the direction transverse to the web length not greater than 0.007 inch, and preferably, 0.004 to 0.006 inch, and are substantially invisible to the naked eye. The height of the projections 27 and 27*a*, that is the amount that they extend from the main body of the label 10 and the depth of the gaps 27*b* depends, of course, on where the ties 24 tear when the label 10 is removed from the web. Thus, the height and the depth can range from zero to one-half of the width W of the perforation 12. However, due to the small length $L_2$ of the projections 27 and 27*a* and the gaps 27*b*, they are substantially invisible to the naked eye.

Therefore, the edges of a label 10 which are formed as described will have an appearance substantially the same as a label which has been cut by a die with a continous cutting edge.

As a practical matter, teeth cannot be formed with the required number per inch on a base plate 23 with a height h more than about 0.006 inch. Therefore, if a height h more than about 0.006 inch is required, the teeth are formed on the edge of a rule on which the teeth can have a height h of about 0.010 inch. When the teeth have a height h for deep perforation cut, i.e. for thicker web stock, the number of teeth should be about 70 per inch for teeth 0.007 high and about 50 per inch for teeth 0.010 high.

Figure 17:
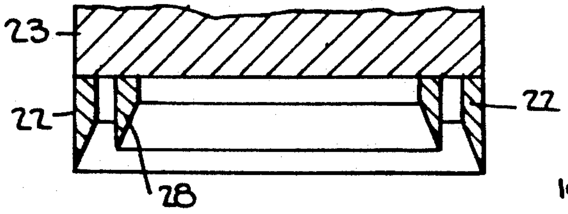
FIG. 17 is an end elevation view of a multi-level die for forming the labels shown in FIGS. 5 and 6.

FIG. 17 illustrates, schematically and in cross-section, a two-level perforating and cutting die which can be used in connection with the embodiment shown in FIGS. 5 and 6. As shown in FIG. 17, the die has outer rows of teeth 22, 22*a* or 22*b*, dimensioned and shaped as described in connection with FIGS. 7–13 and an inner continuous cutting edge 28 which extends from the base 28 by an amount less than the teeth 22 so that the edge 28 will cut the web from which the label portions 19 are formed and not cut the web 20 which is perforated by the teeth 22. However, the continuous cutting edge 28 can be replaced by similar teeth 22 of a height less than the height of the teeth 22 in the outer rows.

In the various embodiments where the side edges of the label portions 10 are within the borders of the web, e.g. FIG. 3, the side edges may be formed either by perforating teeth or a continuous cutting edge. Similarly, the corners of a label portion 10 may be produced by a continuous cutting edge rather than by perforating teeth.

Although preferred embodiments of the present invention have been described and illustrated, it will be apparent to those skilled in the art that various modifications may be made without departing from the principles of the invention.

What is claimed is:

1. A perforated label web comprising:

an elongated web having an upper surface and a lower surface and including a plurality of label portions of the desired label shape disposed, relative to each other, in a first direction in the direction of the length of the web;

said label portions being secured to each other by a plurality of ties disposed and spaced from each other in a second direction transverse to said length of said web, said ties having sufficient strength to prevent said label portions from falling out of said web and to permit pulling of said web in the said direction without rupturing said ties;

said ties being present in number in the range from 20 to 120 per inch in said second direction and each tie having a width dimension in said second direction not greater than 0.007 inch;

said web having a perforation intermediate pairs of adjacent ties which extends from said upper surface of said web to said lower surface of said web and the sum of the lengths of the perforations in said second direction being at least equal to 50% of the length of the label portion in said second direction; and said web being without a carrier web at said lower surface.

2. A perforated label web as set forth in claim 1 wherein said dimension of each said tie is in the range from 0.004 inch to 0.006 inch.

3. A perforated label web as set forth in claim 2 wherein there are at least 50 ties per inch but not more than 120 ties per inch.

4. A perforated label web as set forth in claim 3 wherein the dimension of said ties in the first-mentioned said direction not greater than 0.014 inch.

5. A perforated label web as set forth in claim 1 wherein there are further said ties at the edges of the label portions which extend outwardly from said edges in said second direction.

6. A perforated label web as set forth in claim 1 further comprising a further web engaging said upper surface of the first-mentioned said web, said further web having a plurality of further label portions thereon in registry with the first-mentioned said label portions.

7. A perforated label web as set forth in claim 6 wherein said further label portions are fully cut along their peripheries and are adhesively and removably secured to said upper surface of the first-mentioned said web.

8. A perforated label web as set forth in claim 1 wherein each said perforation has the shape of an I with the segment thereof interconnecting the end segments thereof extending in said second direction.

9. A label of a perforatable material, said label having spaced portions of said material at at least a portion of its periphery, said spaced portions having a width dimension in the direction of said periphery not greater than 0.007 inch and having a dimension transverse to said periphery not greater than 0.014 inch and being present in number in the range from 20 to 120 per inch and the sum of the lengths of the spaces between said spaced portions being at least equal to 25% of said portion of said periphery.

10. A label as set forth in claim 9 wherein said width dimension is in the range from 0.004 to 0.006 inch.

11. A label as set forth in claim 10 wherein there are at least 50 spaced portions per inch but not more than 120 spaced portions per inch.

12. A label as set forth in claim 9 wherein said label has a lower surface for securing the label to an object and an upper surface and further comprising a further label removable secured to said upper surface.

13. A label as set forth in claim 12 wherein the periphery of said further label is without spaced portions.

14. A perforated label web as set forth in claim 1 wherein each said tie has said width dimension substantially throughout its length in said first direction.

15. A label of a perforatable material as set forth in claim 9 wherein said spaced portions have a substantially constant width dimension.

* * * * *

UNITED STATES PATENT AND TRADEMARK OFFICE

CERTIFICATE OF CORRECTION

PATENT NO. : 5,240,755

DATED : August 31, 1993

INVENTOR(S) : Zimmer

It is certified that error appears in the above-identified patent and that said Letters Patent is hereby corrected as shown below:

Col. 4, line 51, insert --stock-- after "paper"

Col. 6, line 61, insert --is-- after "direction"

Col. 8, line 11, change "removable" to --removably--.

Signed and Sealed this

Fifteenth Day of March, 1994

Attest:

Bruce Lehman

BRUCE LEHMAN

*Attesting Officer*

*Commissioner of Patents and Trademarks*